United States Patent [19]

Davenport

[11] Patent Number: 4,665,215

[45] Date of Patent: May 12, 1987

[54] PROCESS FOR PRODUCING 4-ACETOXYBENZOIC ACID

[75] Inventor: Kenneth G. Davenport, Corpus Christi, Tex.

[73] Assignee: Celanese Corporation, New York, N.Y.

[21] Appl. No.: 779,896

[22] Filed: Sep. 25, 1985

Related U.S. Application Data

[63] Continuation-in-part of Ser. No. 633,831, Jul. 24, 1984, abandoned.

[51] Int. Cl.$^4$ .................... C07C 69/017; C07C 65/03; C07C 67/08; C07C 51/245
[52] U.S. Cl. .................................. 560/130; 562/421; 562/475
[58] Field of Search ................ 562/421, 475; 560/138, 560/139, 141, 130

[56] References Cited

U.S. PATENT DOCUMENTS

| | | |
|---|---|---|
| 2,673,217 | 3/1954 | Hull .................. 562/421 X |
| 2,952,703 | 9/1960 | McKeever et al. ............... 562/421 |
| 2,995,598 | 8/1961 | Bauer .................. 560/130 |
| 3,014,961 | 2/1961 | Nelles et al. ............. 562/421 X |
| 3,539,592 | 11/1970 | Crowther et al. ............... 562/421 X |

OTHER PUBLICATIONS

Kobayashi et al., Chem. Abst., vol. 66, Abstract No. 655236z, 1967.
Kato et al., Chem. Abst., vol. 85, Abstract No. 5360g, 1976.
Grant, ed., Hackh's Chemical Dictionary 4th ed., 1969 p. 687.
McOmie, ed., Protective Groups in Organic Chemistry, 1973, pp. 171–182.

*Primary Examiner*—Natalie Trousof
*Assistant Examiner*—Patricia M. Scott
*Attorney, Agent, or Firm*—D. R. Cassady; M. Turken

[57] ABSTRACT

A process is provided for the production of 4-acetoxybenzoic acid by subjecting phenyl acetate to a Fries rearrangement or phenol and an acetylating agent to a Friedel-Crafts acetylation to form 4-hydroxyacetophenone which is then acetylated with an acetylating agent such as acetic anhydride to form 4-acetoxyacetophenone. The 4-acetoxyacetophenone is then oxidized with oxygen in the presence of manganese cations and acetic acid as catalysts and a co-reductant or promoter to form 4-acetoxybenzoic acid. The acetylation of the 4-hydroxyacetophenone has the effect of "masking" the hydroxyl group of the latter compound in a manner necessary to effect the subsequent oxidation of the ketone group of the 4-acetoxyacetophenone.

7 Claims, No Drawings

PROCESS FOR PRODUCING 4-ACETOXYBENZOIC ACID

This application is a continuation-in-part of application Ser. No. 633,831, filed July 24, 1984, now abandoned.

This invention relates to an integrated process for the production of 4-acetoxybenzoic acid from phenyl acetate or phenol and an acetylating agent such as acetic acid or acetic anhydride as the starting material.

BACKGROUND OF THE INVENTION

It is known to prepare 4-acetoxybenzoic acid (4-ABA) by reacting phenol with an alkali metal hydroxide, e.g., potassium hydroxide, to form an alkali metal phenoxide, e.g., potassium phenoxide, and reacting the phenoxide with carbon dioxide in a Kolbe-Schmitt reaction followed by acidic workup to form 4-hydroxybenzoic acid (4-HBA). The acid is then acetylated with an acetylating agent, e.g., acetic anhydride, to form the 4-ABA. A substantial disadvantage of this process is the necessity to neutralize the hydroxybenzoate salt in the course of the Kolbe-Schmitt reaction resulting in the formation of a waste alkali metal salt which must be separated and disposed of.

The preparation of hydroxy aromatic ketones by the Fries rearrangement of aromatic esters is well-known in the art. Thus, Lewis, U.S. Pat. No. 2,833,825 shows the rearrangement of phenyl or other aromatic esters to acylphenols or other hydroxy aromatic ketones using anhydrous hydrogen fluoride as catalyst. The examples of this patent are limited to the rearrangement of esters of higher fatty acids with the yields ranging from 55 to 95%.

Simons et al., *Journal of the American Chemical Society*, 62, 485 and 486 (1940) show the use of hydrogen fluoride as a condensing agent for various rearrangements and at page 486 show the Fries rearrangement of phenyl acetate to obtain p-hydroxyacetophenone.

Dann and Mylius in a dissertation included as part of a series of Reports from the Institute for Applied Chemistry of the University of Erlangen, received for publication on January 7, 1954 and published in *Annalen der Chemie*, 587, 1 to 15, show the rearrangement of phenyl acetate in hydrogen fluoride to 4-hydroxyacetophenone, with a maximum yield of 81% after 24 hours of reaction time, and report a yield of 92% stated to be obtained by K. Weichert as reported in *Angewandte Chemie*, 56, 338 (1943). However, Dann and Mylius suggest that the difference in yields may be at least partly due to the previous ignoring by Weichert of the accompanying 2-hydroxyacetophenone. Dann and Mylius also report somewhat lower yields of hydroxy aromatic ketones from rearrangements in hydrogen fluoride of m-cresyl acetate, p-cresyl acetate, and guaiacol acetate.

Dann and Mylius also disclose the reaction of phenol and glacial acetic acid in the presence of hydrogen fluoride to produce 4-hydroxyacetophenone in a yield of 61.6%. This reaction may be conventionally characterized as a Friedel-Crafts acetylation of phenol with acetic acid as the acetylating agent.

Simons et al., *Journal of the American Chemical Society*, 61, 1795 and 1796 (1939) teach the acylation of aromatic compounds using hydrogen fluoride as a condensing agent and in Table 1 on page 1796 show the acetylation of phenol with acetic acid to produce p.hydroxyacetophenone in 40% yield.

Meussdoerffer et al., German Offenlegungsschrift No. 26 16 986 published Oct. 27, 1977 and assigned to Bayer AG, disclose the acylation of phenolic compounds such as phenol itself with an acyl halide such as acetyl chloride to form hydroxy aromatic ketones.

Khandual et al., *J. Indian Chem. Soc.*, 49, 557-560 (Eng.) (1972) as abstracted in *C.A.* (1972), 77, 125628g, show the oxidation of acetophenone in 95% acetic acid by manganic acetate to form benzoic acid, and formaldehyde. The oxidation of acetophenone containing ring substituents, e.g., methoxy, is also taught.

Den Hertog et al., *Journal of Catalysis*, 6, 357-361, (1966) show the manganic acetate catalyzed oxidation of acetophenone and acetophenone containing any of various ring substituents such as methyl to benzoic acid and corresponding ring substituted benzoic acids.

Van Helden et al., *Rec. Trav. Chim.*, 80, 57-81, (1961) show the manganese ion-catalyzed oxidations of acetophenone and various ring-substituted acetophenones to the corresponding benzoic acids and the cobalt ion-catalyzed oxidation of acetophenone to benzoic acid.

Misra et al., *J. Indian Chem. Soc.*, 52, 1053-1055 (Eng.) (1975) as abstracted in *C.A.* (1976), 84, 150041n, show the vanadium-catalyzed oxidation of acetophenone and acetophenones containing any of various ring substituents such as methoxy.

Nippon Kayaku Co., Ltd. (inventors Susumu Nagao and Toshio Takahashi), Japanese Kokai No. Sho 54(1979) - 109941, discloses and claims the oxidation of esters of m-cresol with oxygen in the presence of a heavy metal salt in a solvent of a low molecular weight fatty acid and/or anhydride. It is clear from the published application that the presence of the acid anhydride was not critical to the reaction.

McKeever and Freimiller, U.S. Pat. No. 2,952,703, teaches the oxidation of acetophenone to benzoic acid with oxygen in the presence of a manganese salt, a carboxylic acid, and nitric acid of from 80°-107° C.

Hull, U.S. Pat. No. 2,673,217, teaches the use of aldehydes as co-reductants in the oxidation reaction.

Crowther et al., U.S. Pat. No. 3,539,592, teach the use of a co-reductant, as for example of an aldehyde, in the substantial absence of metal catalyst.

Other references pertinent to the oxidation of alkyl and acyl side chains to an acid moiety include:

Kato et al., Japanese Pat. No. 75 35,066 issued Nov. 13, 1975 as abstracted in *C.A.* (1976), 85, 5360g; Kobayashi et al., Japanese Pat. No. 67 849 issued Jan. 18, 1967 and abstracted in *C.A.* (1967), 66, 55236z; and Sangaiah et al., *Synthesis* 12, 1018-1019, (1980) all show the transition metal-catalyzed oxidation of p-cresyl acetate to 4-acetoxybenzoic acid.

SUMMARY OF THE INVENTION

In accordance with this invention, 4-acetoxybenzoic acid (4-ABA) is produced from phenyl acetate, or phenol and an acetylating agent such as acetic acid or acetic anhydride by means of an integrated process in which the phenyl acetate, or phenol and an acetylating agent, is first converted to 4-hydroxyacetophenone (4-HAP) by a Fries rearrangement or Friedel-Crafts acetylation respectively. The 4-HAP is then acetylated with an acetylating agent to produce 4-acetoxyacetophenone (4-AAP) which is oxidized with oxygen in the presence of transition metal ions and a co-reductant to produce 4-acetoxybenzoic acid (4-ABA). The 4-ABA may be used as is or may be hydrolyzed in acid solution to 4-hydroxybenzoic acid (4-HBA).

Although the reaction of phenol and an acetylating agent is characterized herein as a "Friedel-Crafts acetylation," no opinion as to the mechanism of reaction should be implied by this characterization.

When carrying out the process of this invention using phenyl acetate as the starting material, the initial Fries rearrangement to produce 4-hydroxyacetophenone (4-HAP) from phenyl acetate is defined by equation (I):

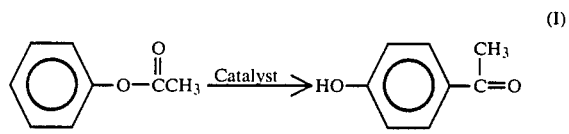
(I)

If phenol and an acetylating agent are used as the starting material, the resulting acetylation reaction to form 4-HAP is indicated by equation (II):

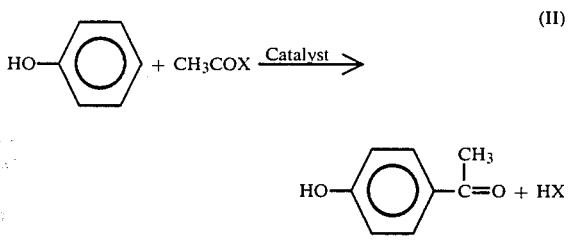
(II)

where X is the residue minus an acetyl group of compounds which are known acetylating agents. For example, X may be, hydroxy, acetoxy, or halide including fluoride, chloride, or bromide. Acetylating agents which may be used are for example, acetic acid, acetic anhydride, acetyl fluoride, acetyl chloride, and acetyl bromide.

The formation of 4-acetoxyacetophenone (4-AAP) from 4-hydroxyacetophenone (4-HAP) using acetic anhydride as the acetylating agent, proceeds as in equation (III):

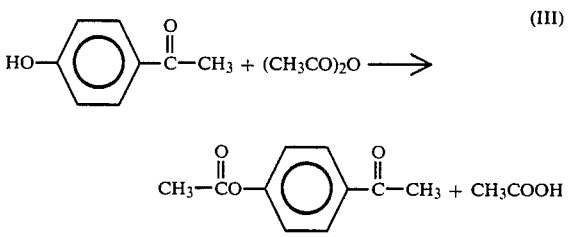
(III)

The formation of 4-acetoxybenzoic acid (4-ABA) by the oxidation of 4-acetoxyacetophenone (4-AAP) proceeds as in equation (IV):

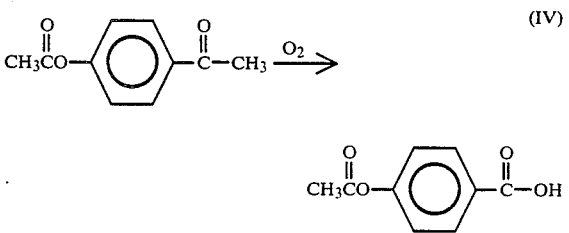
(IV)

If it is desired to hydrolyze the 4-ABA to 4-hydroxybenzoic acid (4-HBA), the reaction proceeds as in equation (V):

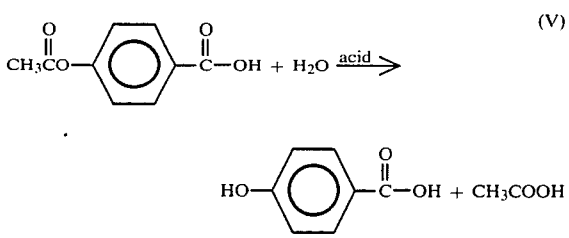
(V)

The acetylation of the hydroxy radical of the 4-HAP has the effect of "masking" such hydroxy radical in a manner necessary for the operability of the subsequent transition metal-catalyzed oxidation of the ketone group of the 4-HAP to produce the 4-ABA in accordance with the invention.

The Fried rearrangement or Friedel-Crafts catalyst used in the production of 4-HAP may be hydrogen fluoride or any other catalyst known in the art to be effective for the Fries or Friedel-Crafts reaction, e.g., aluminum chloride, zinc chloride, or boron trifluoride. In carrying out the reaction, the phenyl acetate, or phenol and acetylating agent, e.g., acetic acid or acetic anhydride, catalyst, and if desired when phenyl acetate is the starting material, an additive for the reaction such as acetic anhydride or acetic acid, may be charged to a corrosion-resistant reactor and the mixture maintained at a temperature, for example, of about 20° to 150° C. for a period, for example, of about ½ to about 4 hours, at a pressure, for example, of about 25 to about 500 psig. If HF is used as the catalyst it may be charged as a liquid or a gas using technologies of handling well-known to those skilled in the art. In carrying out the reaction, an inert gas such as nitrogen may be used to keep the reaction space under the desired pressure and sufficient HF in contact with the reacting liquid. An excess of HF is generally used, for example, about 7 to about 75 moles per mole of phenyl acetate or phenol initially present in the reaction zone.

The 4-acetoxyacetophenone (4-AAP) used as the starting material for the catalytic oxidation to 4-acetoxybenzoic acid may be obtained as a co-product with the 4-hydroxyacetophenone (4-HAP) produced by the Fries rearrangement of phenyl acetate or the Friedel-Crafts acetylation of phenol, e.g., when the reaction is carried out in the presence of HF and an acid anhydide, or it may be produced from the 4-HAP by reacting the latter with an acetylating agent such as acetic anhydride, as indicated by equation (III), by contacting the 4-HAP with, for example, about 1 to 5 moles of the anhydride per mole of 4-HAP at a temperature, for example, in the range of 120° to 140° C. for a period, for example, in the range of 1 to 4 hours.

The 4-acetoxyacetophenone (4-AAP) is oxidized to a 4-acetoxybenzoic acid (4-ABA) as indicated by equation (IV) by subjecting the 4-AAP to a catalytic oxidation with oxygen.

I have found that the reaction is not so general as one would expect in reviewing the prior art cited above. I have found that a lower-alkyl carboxylic acid anhydride is necessary for the reaction to proceed. I have also found that a concentration ratio of anhydride to ketone of from about 0.5:1 to about 5:1 is preferred and that the best conversion to acid with minimal impurities occurs when the anhydride to ketone concentration ratio is from about 1:1 to about 3:1.

Further, I have found that a soluble salt of the manganese cation must be present in the reaction. Other metal cations commonly known as transition element cations may also be present. The transition element cations particularly useful for the process of this invention are the cations of cobalt, chromium, iron, vanadium, tungsten, and molybdenum.

The convenient anion useful to form a soluble salt of these cations is the anion form of the carboxylic acid used as a solvent for the present reaction.

Although it is possible to carry out the procedure of the present invention in the absence of a solvent, the preferred method is to use a lower alkyl carboxylic acid solvent. It is most convenient to use the same carbon skeleton for the acyloxy function on the ketone, the lower-alkyl carboxylic acid solvent, the lower alkyl carboxylic acid anhydride, and the anion moiety of the catalyst salt.

Thus, in the manufacture of 4-acetoxybenzoic acid it is convenient to use acetic acid as a solvent, acetic anhydride as the lower alkyl carboxylic acid anhydride, and manganese acetate as the catalyst.

I have found that either a co-reductant or a promoter is necessary to maintain the reaction. The term co-reductant is used to denote a material which is capable of being oxidized along with the desired reactant. If the concentration of the acyloxy aromatic ketone is sufficiently high, >25%, in a solvent-diluted reaction, the compound acts as its own coreductant. As the oxidation proceeds, however, and the concentration is reduced, it has been found necessary to add another material to the reaction mixture to maintain an efficient oxidation rate.

Useful co-reductants are such compounds as lower alkyl aldehydes and dilower alkyl ketones; as for example, acetaldehyde, propionaldehyde, butyraldehyde, acetone, methyl ethyl ketone, diethyl ketone, methyl isopropyl ketone, and the like.

The term promoter is used to denote a salt which acts as a free radical transfer agent. Of particular use are the salts of bromide anion, i.e., ammonium bromide and the alkali metal bromides: lithium bromide, sodium bromide, and potassium bromide.

According to the teaching of this invention, the oxidation can occur in the presence of (1) a sufficiently high concentration of the acyloxy aromatic ketone, (2) added coreductant, (3) added promoter, (4) 1 (above) then 2 (above), (5) 2 (above) and 3(above), or (6) 1 (above) and 3 (above) then 2 (above).

Oxygen or an oxygen-containing gas is fed into the reaction preferably at such a rate that the amount of oxygen in the vent gas from the reactor does not exceed the level at below which a flammable mixture is attained.

The reaction may be carried out by agitating the reaction mixture at a temperature, for example, of about 90 to about 225° C., preferably about 125° to 175° C., at a pressure for example, of about 100 to 1200 psig, preferably about 200 to 400 psig, for a period, for example, of about 1 to 5 hours, preferably 2 to 4 hours. The catalyst may be used in an amount, for example of about 1 to 2000 ppm preferably about 50 to 1200 ppm, and the co-reductant in an amount, for example of about 5 to 100 mole percent, preferably about 20 to 50 mole percent based on the 4-AAP. The oxygen is added in a manner, as by adequate sparging, to effect a high degree of contact with and mass transfer to the liquid reaction mixture.

The transition metal ions may be added, for example, in the form of a salt of the same alkanoic acid used as the solvent, e.g., as the acetate salt when acetic acid is the solvent. In general, the reaction can be carried out to high conversion of the 4-acetoxyacetophenone to all products with a selectivity to 4-acetoxybenzoic acid, of at least 50%.

The 4-ABA produced by the process of this invention may be used as such or it may be hydrolyzed to 4-HBA as indicated by equation (V), e.g., by refluxing with an aqueous strong acid such as sulfuric, acid.

DESCRIPTION OF SPECIFIC EMBODIMENTS

The following examples further illustrate the invention.

EXAMPLE 1

This example illustrates the preparation of 4-hydroxyacetophenone by the Fries rearrangement of phenyl acetate using hydrogen fluoride as catalyst.

To a 300 cc Hastelloy C autoclave was charged 40.8 g (0.3 mol) of phenyl acetate. The autoclave was sealed, immersed in a dry ice/isopropanol bath and cooled internally to −45° C., and evacuated to ca. 100 Torr. Addition of 120 g (6.0 mol) of anhydrous hydrogen fluoride was performed in a manner such as that the internal temperature of the autoclave did not exceed 0° C. The internal pressure of the reactor was then adjusted to 0 psig with nitrogen. The contents of the autoclave were stirred and heated to 75° C. for 1 h. The hydrogen fluoride was vented over a 45 min period at ca. 45° C. The mixture was poured onto 25 g of ice and neutralized with 45% potassium hydroxide solution. The aqueous mixture was extracted with ethyl acetate. The organic fraction was then dried over anhydrous magnesium sulfate, filtered, and the solvent was removed on a rotary evaporator to yield 44.0 g of a dark green solid corresponding to 99.9% conversion of phenyl acetate and 94.3% selectivity to 4-hydroxyacetophenone.

EXAMPLE 2

This example illustrates the preparation of 4-hydroxyacetophenone by the Fries rearrangement of phenyl acetate using hydrogen fluoride as catalyst with acetic anhydride as additive.

To a 300 cc Hastelloy C autoclave were added 30.6 grams (0.3 mole) of acetic anhydride. The autoclave was cooled to −50° C. and evacuated to 5 Torr whereupon 120 g (6.0 mole) of anhydrous hydrogen fluoride was transferred from a cylinder to the autoclave. After the transfer of hydrogen fluoride was completed, the internal temperature and the internal pressure of the autoclave was adjusted to −50° C. and 0 psig using nitrogen, respectively. To the stirred autoclave was added 81.6 g (0.6 mol) of phenyl acetate at such a rate that the temperature of the mixture did not exceed −23° C. Upon completion of phenyl acetate addition, the contents were warmed to 50° C and stirred for 3 h during which time a pressure of ca. 40 psig was generated. At the end of the run, the hydrogen fluoride was vented through a caustic scrubber and the contents of the autoclave were poured onto ca. 30 g of ice. The pH of the mixture was adjusted to 6.5 using 45% potassium hydroxide and the mixture was then extracted with 75 ml of ethyl acetate (3x). The organic solution was dried over anhydrous magnesium sulfate, filtered, and the solvent was removed using a rotary evaporator.

The reaction proceeded with 98.1% conversion of phenyl acetate and with the following selectivities: phenol 1%; 4-hydroxyacetophenone (4-HAP) 82.3%; 2-hydroxyacetophenone (2-HAP) 4.3%; 3-hydroxyacetophenone (3-HAP) 0.1%; 4-acetoxyacetophenone (4-AAP) 3.8%; and 4-(4'-hydroxyphenyl)acetophenone (HPAP) 0.4%.

EXAMPLE 3

This example describes the formation of 4-hydroxyacetophenone by the Fries rearrangement of phenyl acetate using hydrogen fluoride as catalyst and acetic acid as additive.

The procedure for Example 2 was repeated except that 18 grams (0.3 mole) of acetic acid rather than acetic anhydride were charged to the reactor before it was cooled and charged with the hydrogen fluoride. A conversion of 99.0% of phenyl acetate was obtained with the following selectivities: phenol 3.3%; acetic acid 0.8%; 4-HAP 80.8%; 3-HAP 0; 2-HAP 5.8%; 4-AAP 0.3%; and HPAP 0.3%.

EXAMPLE 4

This example illustrates the preparation of 4-hydroxyacetophenone (4-HAP) by the Friedel-Crafts acetylation of phenol with acetic acid as the acetylating agent.

To a 300 cc Hastelloy C autoclave were charged 9.4 g (0.1 mol) of phenol and 12.0 g (0.2 mol) of acetic acid. The autoclave was sealed, internally cooled to −20° C., and evacuated to 150 Torr, whereupon 100 g (5.0 mol) of anhydrous hydrogen fluoride were transferred from a cylinder to the autoclave. The contents of the autoclave were heated to 80° C. and maintained at that temperature for 1 hour. The contents of the autoclave were then cooled to ca. 20° C. and the hydrogen fluoride was vented to a potassium hydroxide scrubber. Ethyl acetate was added to the contents of the autoclave and the resulting solution was neutralized with a 45% solution of potassium hydroxide. The organic phase was separated, dried over anhydrous magnesium sulfate, and filtered. The solvent was removed on a rotary evaporator to afford 13.1 g (96% yield) of crystalline 4-HAP.

EXAMPLE 5

This example illustrates the preparation of 4-hydroxyacetophenone by the Friedel-Crafts acetylation of phenol with acetic anhydride as the acetylating agent.

To a 300 cc Hastelloy C autoclave cooled to −20° to °C. and evacuated to 50 Torr was added 150 g (7.5 mole) of anhydrous hydrogen fluoride. The content of the autoclave was warmed to 50° C. resulting in an internal pressure of 25 psig. A solution of 23.5 g (0.25 mole) of phenol and 25.5 g (0.25 mol) of acetic anhydride was added to the autoclave over a 3 minute period causing the pressure to drop to 14 psig. The solution was stirred for 1 hour at 50° C. whereupon the hydrogen fluoride was vented at the reaction temperature. The contents of the autoclave were poured onto ice and the aqueous phase was adjusted to pH - 6.0 with a 45% solution of potassium hydroxide. The aqueous phase was extracted with 75 mL of ethyl acetate (3x); the organic fractions were combined, dried over anhydrous magnesium sulfate, and filtered. The reaction proceeded with 99% conversion based on phenol and 95% selectivity to 4-hydroxyacetophenone.

The following example illustrates the reaction of 4-hydroxyacetophenone (4-HAP) with acetic anhydride to form 4-acetoxyacetophenone (4-AAP).

EXAMPLE 6

A solution of 136.2 g (1.0 mol) of 4-hydroxyacetophenone and 400 mL of acetic anhydride was heated at reflux for 3 h under a nitrogen atmosphere. The acetic acid and acetic anhydride was distilled overhead in vacuo (39°–41° C., 2.6 mm Hg). The remaining oil was then distilled in vacuo (132° –134° C., 2.0 mm Hg) to yield 169.7 g (95.2%) of white crystals identified as 4-acetoxyacetophenone.

Examples 7 to 10 illustrate the oxidation of 4-acetoxyacetophenone (4-AAP) to 4-acetoxybenzoic acid (4-ABA).

EXAMPLE 7

A 300 cc Hastelloy C autoclave was charged with 17.8 g (0.1 mol) of 4-acetoxyacetophenone (4-AAP), 0.25 g of manganese (II) acetate tetrahydrate, 1.0 g of acetaldehyde, 25 g of acetic anhydride, and 125 g of acetic acid. An oxygen/nitrogen mixture was sparged into the autoclave at 1000 cc/min such that 5% oxygen was maintained in the vent. A 10% acetaldehyde in acetic acid solution was fed at a rate of 3.0 cc/h. The reaction was run at 150° C. and 100 psig for 3 h. using a stirring speed of 1000 rpm whereupon the acetic acid and acetic anhydride were removed on a rotary evaporator to yield orange crystals. The crystals were dissolved in ca. 150 mL of ethyl acetate and the solution was extracted with 100 mL of water (3x). The organic phase was dried over anhydrous magnesium sulfate, filtered, and the solvent was removed on a rotary evaporator to yield 4-acetoxybenzoic acid (4-ABA) at a conversion of 92.7% based on 4-AAP and with 55.1% selectivity to 4-ABA.

EXAMPLE 8, 9, 10, 11

Following generally the procedure of Example 7, 4-acetoxyacetophenone was converted to 4-acetoxybenzoic acid. The reactants, conditions, conversions, and selectivities are reported in the following table.

|  | Example 8 | Example 9 | Example 10 | Example 11 |
| --- | --- | --- | --- | --- |
| 4-acetoxyacetophenone (g) | 35.8 | 49.8 | 71.2 | 71.2 |
| Manganese (II) diacetate 4H$_2$O (g) | 2.5 | 1.0 | 2.0 | 1.0 |
| Acetic anhydride (g) | 40.8 | 48.6 | 69.1 | 58.2 |
| Acetic acid (g) | 176.6 | 101.6 | 58.4 | 70.6 |
| Sodium acetate (g) | 0 | 0.35 | 0 | 0 |
| Air (cc/min) | 1000 (a) | 800 (b) | 800 (c) | 800 (d) |
| Oxygen content at vent (%) | <9.5 | <10.5 | <10.6 | <7.5 |
| Temperature °C. | 130 | 130 | 150 | 110 |
| Pressure (psig) | 400 | 400 | 400 | 400 |
| Stirring rate (rpm) | 1000 | 1000 | 1000 | 1000 |
| Reaction time (min) | 108 | 145 | 180 | 210 |

-continued

|  | Example 8 | Example 9 | Example 10 | Example 11 |
| --- | --- | --- | --- | --- |
| Conversion (%) | 99.9 | 93.8 | 99.4 | 67.5 |
| Selectivity (%) | 85.0 | 88.3 | 76.0 | 73.4 |

(a) Switched to 500 cc/min air and 500 cc/min N2 after 63 minutes.
(b) Switched to 400 cc/min air and 400 cc/min N2 after 50 minutes.
(c) Switched to 400 cc/min air and 400 cc/min N2 after 90 minutes.
(d) Switched to 400 cc/min air and 400 cc/min N2 after 30 minutes.

The 4-ABA of this invention, may be utilized as monomer in the preparation of polymers capable of forming an anisotropic melt phase and suitable for being formed into shaped articles such as molded articles, fibers and films, as shown, for example in U.S. Pat. Nos. 4,339,375; 4,341,688; 4,351,918; and 4,355,132.

As stated, the 4-ABA of this invention, may also be hydrolyzed to form 4-hydroxybenzoic acid (4-HBA) which has many uses in organic syntheses, and as an intermediate for the production of preservatives, dyes and fungicides. The following example illustrates this process.

EXAMPLE 12

A solution of 4.5 g (0.025 mole) of 4-acetoxybenzoic acid, 25 g of dimethoxyethane, 25 g of water, and 6.1 g of concentrated sulfuric acid was heated at reflux for 2 hours under a nitrogen atmosphere. The solution was cooled, saturated with sodium chloride, and extracted with 75 mL of ethyl acetate (3x). The organic fractions were combined, dried over anhydrous magnesium sulfate, and filtered. Rotary evaporation afforded a substantially quantitative yield of 4-hydroxybenzoic acid based on the 4-acetoxybenzoic acid.

I claim:

1. A process comprising contacting phenyl acetate with a Fries Rearrangement catalyst or phenol and an acetylating agent with a Friedel-Crafts catalyst to form 4-hydroxyacetophenone, acetylating the latter with an acetylating agent to form 4-acetoxyacetophenone, and oxidizing said 4-acetoxyacetophenone with oxygen in the presence of a soluble salt of the manganese cation, acetic ahydride and a co-reductant or promoter to form 4-acetoxybenzoic acid.

2. The process of claim 1 wherein said 4-acetoxybenzoic acid is hydrolyzed to form 4-hydroxybenzoic acid.

3. The process of claim 1 wherein hydrogen fluoride is employed as the Fries Rearrangement Catalyst or the Friedel-Crafts catalyst.

4. The process of claim 3 wherein the Fries rearrangement of phenyl acetate is employed to produce 4-hydroxyacetophenone as the first step in the process.

5. The process of claim 3 wherein the Friedel-Crafts acetylation of phenol with an acetylating agent is employed to produce 4-hydroxyacetophenone as the first step in the process.

6. The process of claim 5 wherein both acetylating agents are acetic anhydride.

7. The process of claim 6 wherein said co-reductant is acetaldehyde.

* * * * *